US005681902A

United States Patent [19]
May

[11] Patent Number: 5,681,902
[45] Date of Patent: Oct. 28, 1997

[54] PROCESS FOR THE PERFLUOROALKYLATION OF SUBSTANCES HAVING TERMINAL UNSATURATION

[75] Inventor: Donald Douglas May, Chadds Ford, Pa.

[73] Assignee: E. I. Du Pont de Nemours and Company, Wilmington, Del.

[21] Appl. No.: 585,047

[22] Filed: Jan. 11, 1996

[51] Int. Cl.$^6$ .................................................... C08F 8/24
[52] U.S. Cl. ........................ 525/359.1; 525/327.4; 525/333.2; 570/123; 570/126; 570/134; 570/135; 570/136
[58] Field of Search .................. 525/359.1; 570/123, 570/126, 134, 135, 136

[56] References Cited

U.S. PATENT DOCUMENTS

| | | | |
|---|---|---|---|
| 3,283,012 | 11/1966 | Day | 260/633 |
| 3,378,609 | 4/1968 | Fasick et al. | 260/890 |
| 3,462,296 | 8/1969 | Raynolds et al. | 117/161 |
| 3,491,169 | 1/1970 | Raynolds et al. | 260/900 |
| 3,842,053 | 10/1974 | Villa et al. | 260/83.3 |
| 3,923,715 | 12/1975 | Dettre et al. | 260/29.6 R |
| 3,952,066 | 4/1976 | Glickman et al. | 260/615 BF |
| 4,346,141 | 8/1982 | Remington | 428/289 |
| 4,595,518 | 6/1986 | Raynolds et al. | 252/8.6 |
| 4,958,039 | 9/1990 | Pechhold | 556/421 |
| 5,097,090 | 3/1992 | Beck | 568/842 |
| 5,408,010 | 4/1995 | May | 525/327.4 |
| 5,427,859 | 6/1995 | May | 428/421 |

FOREIGN PATENT DOCUMENTS

| | | |
|---|---|---|
| 2336913 | 7/1974 | Germany . |
| 49069605 | 5/1979 | Japan . |
| 56125394 | 3/1993 | Japan . |

*Primary Examiner*—Bernard Lipman

[57] ABSTRACT

Free radical reaction of unsaturated material, dissolved in a polar, water immiscible organic solvent, & perfluoroalkyl iodide in the presence of buffer or means for adjusting pH of aqueous phase.

10 Claims, No Drawings

PROCESS FOR THE PERFLUOROALKYLATION OF SUBSTANCES HAVING TERMINAL UNSATURATION

FIELD OF THE INVENTION

This invention relates to an improved process for the synthesis of novel perfluoroalkyl-substituted derivatives of compounds and polymers having terminal olefinic or acetylenic unsaturation. Such derivatives have utility as oil-and water-repellents and soil-resist agents for nylon carpets.

BACKGROUND OF THE INVENTION

Several of the currently-used oil-, water-, and soil-repellent agents for nylon carpets are based on compounds and polymers derived from perfluoroalkylethyl alcohols. The perfluoroalkylethyl alcohols can be prepared from by reacting perfluoroalkyl iodides sequentially with ethylene to form the corresponding perfluoroalkylethyl iodides, then with oleum to form perfluoroalkylethyl sulfates, followed by conversion to the perfluoro-alkylethyl alcohols by hydrolysis. The perfluoroalkylethyl alcohols are then incorporated into compounds or polymers for application to a fiber substrate.

The processes based on the preparation of fluoroalkylethyl alcohols from fluoroalkyl iodides have significant drawbacks. They involve several steps in which the expensive fluorocarbon moiety is subject to yield and handling losses; pressure equipment is required for some of the steps; and for every pound of fluoroalkylethyl alcohol formed, about two pounds of by-product sulfuric acid are formed and require disposal. It would be desirable if a suitable polymeric fluorocarbon-derived soil-resist could be prepared more directly from the fluoroalkyl iodides with out the disadvantages of the currently used multiple-step technology needed to form the fluoroalkylethyl iodide and the fluoroalkylethyl alcohol.

BRIEF SUMMARY OF THE INVENTION

The present invention relates to an process for the facile addition of perfluoroalkyl groups to an unsaturated organic compound or an unsaturated polymer. In this process, a unsaturated compound or polymer, in solution in a polar and water-immiscible organic solvent, is reacted with perfluoroalkyl iodide in the presence of a free radical initiator and either an aqueous buffered solution or an aqueous solution with a means for continuously measuring and adjusting the pH of the aqueous phase with a base. After reaction, the organic phase, essentially free of the by-product hydrogen iodide, contains the perfluoroalkyl-substituted compound or polymer for subsequent redispersion in water and application as an oil-, water-, and/or soil-repellent agent.

DETAILED DESCRIPTION OF THE INVENTION

The process of this invention involves perfluoroalkylation of a compound or polymer which contains terminal olefinic or acetylenic groups, exemplified by, but not limited to, the following compounds and polymers with unsaturation: polybutadiene. butadiene copolymers, polymers with vinylic side chains, polymers with allylic side chains, polymers with terminal acetylenic sidechains, and allylically substituted diisocyanates which are new compounds disclosed and claimed in my U.S. patent application filed of even date herewith (Attorney Docket No. CH-2313).

The perfluoroalkylation process of this invention is practiced by dissolving the unsaturated compound or polymer in a polar water-immiscible solvent. Various non-water-soluble solvents can be used, such as ketones, esters and aromatics, their use being dictated by the particular solubility characteristics of the unsaturated compound or polymer. Water immiscible organic solvents which form an azeotrope with water are preferred. For commercial practicality, one would choose a water-immiscible organic solvent which provides a high proportion of the organic solvent in the azeotrope, but that is not essential. Most preferred solvents are those which form convenient azeotropes, such as methyl isobutyl ketone and toluene. Additionally, the solvent must be dry initially if the unsaturated compound or polymer will react with moisture, as is the case with allylically substituted diisocyanate oligomers and polymers. The function of the solvent is to dissolve the unsaturated compound or polymer and the perfluoroalkylated compound or polymer product of the process of this invention, provide a separate phase in the presence of the aqueous buffer or pH-controlled aqueous phase at least at the conclusion of the perfluoroalkylation stage, whereby the hydrogen iodide by-products have been extracted from the organic phase, and can be readily stripped from an aqueous emulsion prepared from the organic phase. The identity of the solvent is not critical so long as it is polar and water-immisible; such solvents are exemplified by, but not limited to, ketones such as methyl isobutyl ketone (4-methyl-2-pentanone) or methyl isoamyl ketone (4-methyl-2-hexanone), hydrocarbons such as toluene or xylene, esters such as ethyl acetate, butyl acetate, or ether-esters such as propylene glycol methyl ether acetate (PMA, 1-methoxy-2-propyl acetate) or the like.

In an embodiment of the invention, to a solution of the unsaturated composition or polymer is added an aqueous buffered solution of pH 2–8, preferably pH of 3–6. As an alternative to the buffered phase, an aqueous phase may be used with a means for continuously measuring the pH of the phase. A Group Ia or Group IIa metal hydroxide (preferably sodium hydroxide) is added to the aqueous phase, either manually or by means of an automated pump controlled by the pH signal, so as to maintain the pH in the range 2–8, and preferably 3–6, during the perfluoroalkylation. Optimally an aqueous buffered solution containing about 5% sodium hydroxide and 10% acetic acid, having a pH of 4, is used. The aqueous buffer or the pH-controlled water phase is essential to this invention as it makes it possible to achieve rapid and complete reaction of the unsaturated compound or polymer with the perfluoroalkyl iodide; thus the buffered or controlled pH phase acts to scavenge the hydrogen iodide eliminated in the perfluoroalkylation step. Too high a pH causes hydrolysis and the formation of inert products such as the perfluoroalkyl hydrides, too low a pH results in incomplete reaction caused by a build up of hydroiodic acid by-product. The amount of buffer required is not critical, generally 0.1 to 1.0 mole equivalents (preferably 0.5 mole equivalents) of base, based on the perfluoroalkyl iodide will suffice. Comparison of Examples 1 & 3 with Comparative Examples 1 & 3 set forth below demonstrates the effect of the buffer on yield. The range of the polymer concentration in the organic solvent solution can be from less than one percent up to the solubility limit of the polymer. The mole ratio of perfluoroalkyl iodide to polymer can range from 0.01 to 0.75, with an optimum range of 0.1 to 0.5. To the stirred two-phase system comprising the organic solvent solution of polymer and the buffered aqueous solution, or the pH-controlled aqueous phase, preferably under an inert gas atmosphere to exclude oxygen and moisture, is immediately added at least one perfluoroalkyl iodide. The perfluoroalkyl iodide may be either a single perfluoroalkyl iodide or a mixture of perfluoroalkyl iodides having the formula $R_fI$. Typically the $R_f$ radical is a straight chain fluoroalkyl residue containing 3 to 20 carbon atoms or a mixture of such iodides may be employed. Preferably, the $R_f$ radical contains about 4 to 16 carbon atoms. The iodide may also include a substituent Y which may be F, Cl, Br or H, although F is preferred. In a more preferred embodiment, one uses a mixture of perfluoroalkyl iodides having the formula:

$$F(CF_2)_aI$$

wherein a is predominantly 6, 8 and 10. In a typical mixture, hereinafter Perfluoroalkyl Iodide Mixture A, the compounds will have the following approximate composition in relation to their $F(CF_2)a$ radicals:

0% to 3% wherein a=4,
27% to 37% wherein a=6,
28% to 32% wherein a=8,
14% to 20% wherein a=10,
8% to 13% wherein a=12,
3% to 6% wherein a=14,
0% to 2% wherein a=16,
0% to 1% wherein a=18, and
0% to 1% wherein a=20.

Other fluorochemical reagents which can be used include a perfluoroalkyl iodide mixture, hereinafter Perfluoroalkyl Iodide Mixture B, of the formula shown below wherein a is predominantly 8, 10 and 12. In a typical mixture of such fluoroalkyl iodides, the compounds will have the following approximate composition in relation to their $F(CF_2)a$ radicals:

0% to 3% wherein a=6,
45% to 52% wherein a=8,
26% to 32% wherein a=10,
10% to 14% wherein a=12,
2% to 5% wherein a=14,
0% to 2% wherein a=16,
0% to 1% wherein a=18, and+
0% to 1% wherein a=20.

After purging with inert gas, to the reaction vessel containing the organic solvent solution of the unsaturated polymer and the perfluoro-alkyl iodide is added an organic peroxide initiator, exemplified by, but not limited to, t-butyl peroctanoate (2-ethylhexaneperoxoic acid, 1,1-dimethylethyl ester, CAS 3006-82-4) or a VAZO® initiator, exemplified by, but not limited to, VAZO®67 (2,2'-azobis [2-methylbutane-nitrile], CAS 13472-08-7) and VAZO®64 2,2'-azobis[2-methylpropane-nitrile, both from DuPont). The amount of the organic peroxide initiator is about 0.1 to 10% (preferably 0.5%), based on the weight of the perfluoroalkyl iodide. The reactants are stirred at a temperature such that the initiator will have a half-life of about 2–4 hours (tables of initiator half lives are provided by initiator manufacturers). A second 0.5% portion of the initiator is added after about three to six hours. One should use a reaction temperature range in which the initiator has a reasonable half life, e.g. 70° C. –110° C. In particular embodiments typical reaction temperatures would be 70°–110° C. for t-butyl peroctanoate (preferably 85°–90° C.) and 60°–100° C. for VAZO®67 (preferably 75°–80° C). Heating and stirring are continued until this step is completed, at which stage the absence of unreacted perfluoroalkyl iodide can be demonstrated by gas chromatography, typically after about 6–14 hours.

The buffered aqueous solution or pH-controlled aqueous phase is essential to this invention in that the initial product of the reaction between the polymeric unsaturated and the perfluoroalkyl iodide is a compound in which a perfluoroalkyl group and an iodine atom are substituted on the adjacent carbon atoms which initially constituted the unsaturated group. The novel aqueous buffered phase or pH-controlled aqueous phase assists in the dehydroiodination of this initial reaction product substantially as the initial product is formed, and by removing the by-product hydrogen iodide also substantially as it is formed in the dehydroiodination step. After reaction, the organic phase, essentially free of the by-product hydrogen iodide, contains the perfluoroalkyl substituted polymer for subsequent redispersion in water and application as an oil-, water-, and/or soil-repellency agent.

When essentially no unreacted $R_fI$ can be detected, the contents of the reaction vessel are transferred to a separatory funnel, or the like, and the bottom aqueous phase, containing the inorganic iodide from the reaction of the perfluoroalkyl iodide with the unsaturated polymer, is removed to leave the perfluoroalkyl-substituted product in solution in organic solvent. If necessary the organic solvent layer can be washed with water to further lower the concentration of iodide remaining in the solvent layer.

In a preferred embodiment, the solvent layer may be converted to a water dispersion for application to carpet by selecting an emulsifying agent by customary techniques such as are described by Rosen in Surfactants and Interfacial Phenomena, Wiley-Interscience, New York, N.Y., 1978. The selected emulsifying agent is added and the mixture emulsified by customary emulsification techniques such as sonnication or homogenization and at a temperature sufficient to insure solubility of the perfluoroalkyl-substituted product in the organic solvent. Examples of preferred emulsifying agents are exemplified by, but not limited to, quaternary ammonium halide, such as ARQUAD®18-50 (N,N,N-trimethyl-1-octadecyl ammonium chloride, CAS 112-03-8, Akzo Chemicals) or ARQUAD®12-50 (N,N,N-trimethyl-1-dodecyl ammonium chloride, CAS 112-00-5, Akzo Chemicals), sulfonates such as SUL-FON-ATE AA®-10 (Sodium dodecylbenzene sulfonate, CAS 25155-30-0, Tennessee Chemical Co.), as well as alcohol ethoxylates such as MERPOL® SE. Emulsification temperatures can be in the range of 40°–90° C., preferably about 60° C. The volatile organic solvent is then stripped from the emulsion by distillation under reduced pressure at about 40°–90° C. (preferably 60° C.) to yield an aqueous dispersion of the soil resist agent. Excessive temperatures during solvent stripping may cause the emulsion to break. The dispersion is standardized by dilution with water to product specifications, typically to a specified fluorine content, and applied to nylon carpet by conventional application techniques to provide 500–1000 ppm fluorine based on the fiber weight, and dried in a forced air oven at 90°–150° C. (preferably 120° C.) for 20–40 minutes (preferably 25 minutes). The treated carpet may be tested for soil resistance by the standard tests referenced in AATCC Method 123–1988.

The products produced by the process of this invention are much more fully perfluoroalkylated than the products of the prior art. A more fully perfluoroalkylated product with higher fluorine content requires lower application rates on the final substrate to give equivalent oil-, water-, and soil-repellent properties. Additionally, the higher fluorine content of the products of this invention enable one to obtain the necessary fluorine content on the treated carpet with less inert polymer backbone. While the inert polymer backbone is essential to carry the perfluoroalkyl side chains, the backbone polymer does not of itself contribute soil repellency.

The following Examples further illustrate the invention.

EXAMPLE 1

Into a 1000 ml 4 neck round bottom flask fitted with mechanical agitator, reflux condenser, thermocouple, and argon sparge tube were dissolved into 300 ml of MIBK, 20 g of a 40/60% styrene-butadiene block copolymer (MBSG-2050, Nippon Soda Co.) containing 90% of the butadiene as 1,2-isomer. To this reaction flask were added 100 ml of an acetate buffer containing 80 g water, 10 g acetic acid and 5 g sodium hydroxide, 45 g of Perfluoroalkyl Iodide Mixture A and two 1.0 g additions of t-butyl peroctanoate initiator. The flask was heated at 90° C. under stirring for 8 hours after which time there was no unreacted perfluoroalkyl iodide. After reaction, a phase cut was taken and the contents washed with 100 ml of 10% sodium hydroxide solution and 100 ml of a concentrated brine solution. The MIBK solution was added to 400 ml of water containing 5 g of trimethyldodecylammonium chloride and homogenized at 3000 psig to give 422 g of an aqueous emulsion of a perfluoroalkyl-substituted styrene-butadiene block copolymer containing 6.0% fluorine, thereby accounting for 43 g of the 45 g perfluoroalkyl iodide originally charged to the reactor.

Comparative Example 1

The reaction described in example 1 was repeated except for the omission of the buffer. After 16 hours reaction at 90° C. with four 0.5 g additions of peroxide initiator at 4 hour intervals, there remained, by quantitative gas chromatography, 40 g of unreacted perfluoroalkyl iodide.

EXAMPLE 2

Into a 1000 ml 4 neck round bottom flask fitted with mechanical agitator, reflux condenser, thermocouple, and Argon sparge tube were placed 300 ml of dry methyl isobutyl ketone (MIBK), and 20 grams of polybutadiene (G-1000, Nippon Soda Co.) with an average molecular weight of 1200 containing 90% 1,2-vinyl pendant or terminal groups. To the same reaction flask were added 100 ml of an aqueous solution containing 85 g water, 5 g sodium hydroxide, and 10 g acetic acid. Also added at this time were 100 g of mixed Perfluoroalkyl IodideMixture A. After purging for 10 minutes, 0.5 g of t-butyl peroctanoate was added. Six hours later another 0.5 g of the peroxide initiator was added under an argon sparge. After 14 hours time from the initial peroxide addition, a sample analyzed by gas chromatography showed no unreacted perfluoroalkyl iodide. The contents the flask were then placed into a separatory funnel and the bottom aqueous layer containing iodide from the reacted perfluoroalkyl iodides was removed. The organic layer was distilled off under reduced pressure (at 60° C. and 100 mm Hg) to leave perfluoroalkyl-substituted polybutadiene (94 g of solids that, by elemental analysis, contained 53% fluorine).

EXAMPLE 3

The preparation of the soil-resist polymers was carried out in a 1 liter resin kettle with bottom outlet, fitted with a 200 rpm mechanical stirrer, a reflux condenser, a thermocouple connected to a PID controller that heats an external resistance heating jacket, and an argon sparge tube; hereafter referred to as Reactor 1. It was charged with 400 g dry methyl isobutyl ketone (MIBK), and 60 g (0.31 eq) of DESMODUR® N-100, (a hexamethylene isocyanate biuret sold by Miles Inc. having the formula:

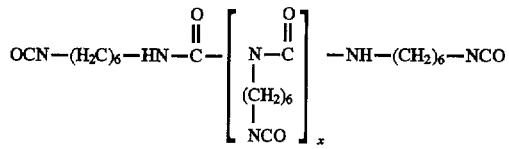

To the resulting MIBK/DESMODUR® mixture were added slowly 30 g (0.30 eq) of diallyl amine (0.30 eq) and the reactor temperature was allowed to go up to 90° C. After addition was complete the contents were stirred for 30 minutes, at which point gas chromatographic analysis showed no unreacted diallyl amine. To the same reaction mixture were added 50 g of a dilute acetate buffer consisting of 5 g concentrated acetic acid, 5 g 50% sodium hydroxide and 40 g water, along with 150 g Perfluoroalkyl Iodide Mixture A. The contents were sparged with nitrogen and, when the temperature of the mixture had again been raised to 90° C., 0.5 g of VAZO®67 was added. After four hours, gas chromatographic analysis showed no unreacted perfluoroalkyl iodide.

The stirring in reactor 1 was turned off and the contents were allowed to settle and a phase cut taken which contained the aqueous buffer. To the reactor, 100 ml of 20% potassium carbonate were added and the contents stirred at 70° C. for 10 minutes. The stirring was stopped, and another phase cut was taken that contained aqueous iodide. The contents in the reactor were washed again with saturated sodium acetate solution. After the phase cut, the organic phase was added to the following system to make a dispersion.

To make an anionic dispersion, the organic solution described above was added to 600 g of water containing 4.5 g of sodium dodecyl benzene sulfonate in a high shear roto-stator mixer. After addition was complete, the emulsion was passed twice through a two stage Gaulin homogenizer at 3000 psig. After homogenization, the emulsion was distilled under reduced pressure to remove MIBK solvent as a water azeotrope (60° C. at 120 mm) to leave 900 g of a cream colored dispersion that contained 9.5% fluorine by weight (total fluorine accountability 97%). The unimodal particle size of this dispersion was 107 nm with an intensity average of 139 nm. The dispersion, made from base hydrolysis of the Perfluoroalkyl Iodide Mixture A adduct, contained 637 ppm iodide.

To make a cationic dispersion, an organic solution similar to the one described above, except containing only 250 g of dry MIBK, were added to 400 g of water containing 4 g each trimethyl dodecylammonium chloride and trimethyl octadecylammonium chloride at 60° C. in a high shear roto-stator mixer. After addition was complete, the emulsion was passed twice through a two stage Gaulin homogenizer at 3000 psig. After homogenization, the emulsion was distilled under reduced pressure to remove MIBK solvent as a water azeotrope (60° C. at 120 mm) to leave 660 g of a cream colored dispersion that contains 13% fluorine by weight (total fluorine accountability 97%). The unimodal particle size of this dispersion was 112 mm.

Other anionic and cationic surfactants were also used. The characteristics of the dispersions were only slightly different. Each sample was diluted and spray applied to 32 oz stain resist treated level loop nylon carpet at 1000 ppm fluorine. An untreated piece of carpet was used as a control, and all three were placed into a forced hot air oven at 250° F. for 25 minutes. The carpet pieces were tested together by the method described by AATCC Method 123–1988 and the pieces treated with cationic and anionic formulations showed improved resistance to soiling compared to the control.

Comparative Example 2

The reaction described in Example 1 was repeated except for the omission of acetate buffer. After 4 hrs reaction at 90° C., a sample was taken and showed 105 g unreacted perfluoroalkyl iodide. An additional 0.5 g of VAZO®67 was added and the contents held at 90° C. for 4 more hours and sampled. There were 100 g of Perfluoroalkyl Iodide Mixture A remaining. Additional amounts of VAZO®67 were added at 4 hour intervals and the contents heated for 24 total hours to leave 50 g of unreacted perfluoroalkyl iodide in solution, compared with no detectable perfluoroalkyl iodide in the case with acetate buffer, showing the benefit in rate and conversion afforded by the buffer.

EXAMPLE 4

Into reactor 1 were placed 60 g (0.31 eq) DESMODUR® N- 100 and 250 g dry MIBK. To the solution were added 20 g (0.20 eq) of diallyl amine and the contents were allowed to heat up to 90° C. and stirred for 30 minutes after addition were complete. Then 5 ml water were added and the same reaction mix for 1 hour. To the same reaction mixture were added 50 g of a dilute acetate buffer consisting of 5 g concentrated acetic acid, 5 g 50% sodium hydroxide and 40 g water, along with 100 g Perfluoroalkyl Iodide Mixture A. The contents were sparged with nitrogen and when the mixture reached 90° C. again from a temperature of about 75° C., 0.5 g of VAZO®67 was added. After four hours, gas chromatographic analysis showed no unreacted perfluoroalkyl iodide. The contents were worked up as described previously and a cationic dispersion was made. The product was tested as described previously and shows better dry soil and oil and water repellency than the untreated control.

EXAMPLES 5–18

The following examples in Table 1 are illustrative but not exhaustive of the possible chain extended isocyanate based soil-resists that can be prepared. In general, the polyisocyanate was dissolved into MIBK solution functionalized with the number of equivalents of diallyl amine indicated in the table. The resultant prepolymer was chain extended using 0.01 wt % dibutyl tin dilaurate catalyst with the difunctional compounds listed in Table 1. The reaction products were worked up, emulsified, and tested as described in Example 1. In general, cationic dispersion soil-resists performed better in the drum soil screen than anionic ones.

TABLE 1

EXAMPLES 3–16

| No. | Isocyanate | Ratio | Extender | Surfactant | Solids |
|---|---|---|---|---|---|
| | Polymer Characteristics | | | Dispersion Characteristics | |
| 3 | N-100 | 0.67 | a | 3% AA-10 | 50/25/1 |
| 4 | N-100 | 0.67 | a | 3% ARQUAD 12/18 | 50/25/1 |
| 5 | N-100 | 0.67 | b | 3% ARQUAD 12/18 | 50/25/1 |
| 6 | N-100 | 0.67 | b | 3% AA-10 | 50/25/1 |
| 7 | N-100 | 0.67 | c | 3% ARQUAD 12/18 | 50/25/1 |
| 8 | N-100 | 0.67 | c | 3% AA-10 | 50/25/1 |
| 9 | N-100 | 0.67 | d | 3% AA-10 | 50/25/1 |
| 10 | N-100 | 0.67 | d | 3% ARQUAD 12/18 | 50/25/1 |
| 11 | N-100 | 0.67 | e | 3% AA-10 | 50/25/1 |
| 12 | N-100 | 0.67 | e | 3% ARQUAD 12/18 | 50/25/1 |
| 13 | N-100 | 0.67 | f | 3% AA-10 | 50/25/1 |
| 14 | N-100 | 0.67 | f | 3% ARQUAD 12/18 | 50/25/1 |
| 15 | N-100 | 0.67 | g | 3% AA-10 | 50/25/1 |
| 16 | N-100 | 0.67 | g | 3% ARQUAD 12/18 | 50/25/1 |

NOTES:
Reactions run in MIBK with the acetate buffer described in Example 1 unless noted.
Initiated with 0.3 wt percent VAZO®67 at 90° C., complete Perfluoroalkyl Iodide Mixture A consumption in 2 hrs.
LEGEND:
Ratio is the mole ratio of diallyl amine to isocyanate, remaining isocyanate reacted with extender Solids= (concentration of polymer in solvent/concentration of solids in the dispersion/ratio of polymer solution to water in emulsion)
EXTENDER DETAIL:

a) JEFFAMINE® D-400 poly[oxy(methyl-1,2-ethanyl)] alpha-(2-aminomethylethyl)-omega-(2-aminomethylethoxy-CAS No. [9146-10]0 (Huntsman Chemical, Houston, Tex.)

b) Extended with Polyacrylate A365 equivalent weight (EW)=607 containing terminal hydroxyl groups c) Extended with Saturated polyester 670A-80 EW=500 containing terminal hydroxyl groups d) Extended with DESMOPHEN®1300 saturated polyester in xylene EW=567 containing terminal hydroxyl groups e) Extended with DESMOPHEN® A- 160A olyacrylate EW=1058 containing terminal hydroxyl groups All of extenders b) through e) are products of the Bayer Corporation, Pittsburgh, Pa.

EXAMPLE 19

Into reactor 1 were placed 60 g of DESMODUR® N-100 and 400 ml MIBK. To this solution were added 18 g of allyl alcohol and 0.1 g dibutyltin dilaurate. The contents were heated at 90° C. for 2 hours. A sample of the reaction mixture was analyzed for unreacted allyl alcohol by quantitative gas chromatography and showed no (<0.5 g) unreacted allyl alcohol.

To the same reaction mass were added, 100 ml of 0.6 M acetate buffer (10 g concentrated acetic acid, 10 g 50% NaOH in 80 ml water), 100 g of Perfluoroalkyl Iodide Mixture A, and 0.5 g of VAZO® 67. There was one more addition of initiator four hours later. After 8 hours heating at 90° C., analysis showed no unreacted perfluoroalkyl iodide. A phase cut was taken, the contents washed with 100 ml concentrated sodium acetate, and the total organic solution was homogenized at 3000 psig in 600 ml water with 2 g trimethyloctadecyl ammonium chloride and 2 g trimethyldodecyl ammonium chloride. After removing the organic solvent, the resultant dispersion was applied onto carpet at 1000 ppm fluorine and gave drum soil performance better than the untreated control.

EXAMPLE 20

The experiment in Example 1 was repeated except DESMODUR® N-3200 was used in place of DESMODUR®

N-100. The reaction mass was emulsified to give 1000 g of an emulsion containing 8.8% Fluorine.

EXAMPLE 21

Reactor 1 was charged with 400 g dry methyl isobutyl ketone (MIBK), and 25 g of hexamethylene diisocyanate. To this were added slowly, 33 g (0.30 eq) of diallyl amine and the pot temperature allowed to go up to 90° C. After addition was complete, the contents were allowed to stir for 30 minutes and gas chromatographic analysis showed no unreacted diallyl amine. To the same reaction mixture were added 50 g of a dilute acetate buffer consisting of 5 g concentrated acetic acid, 5 g 50% sodium hydroxide and 40 g water, along with 150 g Perfluoroalkyl Iodide Mixture A. The contents are sparged with nitrogen and when the mixture reached 90° C. again, 0.5 g of Vazo®67 was added. After four hours, gas chromatographic analysis showed no unreacted perfluoro alkyl iodide.

The mixture was worked-up and emulsified as described in Example 1 to give 756 g of an aqueous emulsion that contained 11.3% fluorine. It was applied to carpet to give soil-resist properties similar to the compound made in Example 1.

I claim:

1. A process for the addition of perfluoroalkyl groups to an unsaturated organic compound or an unsaturated polymer which comprises dissolving an olefinically or acetylenically unsaturated compound or an olefinically or actylenically unsaturated polymer in a water-immiscible polar organic solvent, reacting said dissolved compound or polymer with a perfluoroalkyl iodide in the presence of a free radical initiator and either an aqueous buffered solution or an aqueous solution with a means for continuously measuring and adjusting the pH of the aqueous phase with a base, and recovering a perfluoroalkyl-substituted organic compound or a perfluoroalkyl-substituted polymer from the resulting organic phase, said aqueous buffered solution or said means providing a pH between 2 and 8.

2. The process of claim 1 wherein said pH is between 3 and 6.

3. The process of claim 1 wherein said buffered solution has a pH of 4.

4. The process of claim 1 wherein said solvent is volatile under the reaction conditions.

5. The process of claim 1 wherein said solvent forms an azeotrope with water such that said azeotrope has a high organic content.

6. The process of claim 1 wherein said solvent is a ketone, an ester or an aromatic.

7. The process of claim 1 wherein said solvent is methyl isobutyl ketone, methyl isoamyl ketone, toluene, xylene, ethyl acetate, butyl acetate, or propylene glycol methyl ether acetate.

8. The process of claim 1 wherein said perfluoroalkyl iodide has the formula $F(CF_2)_aI$ wherein a is 4 to 20.

9. The process of claim 8 wherein said a is predominantly 6, 8 and 10.

10. The process of claim 8 wherein said a is predominantly 8, 10 and 12.

* * * * *